US007450724B1

(12) United States Patent
Greminger

(10) Patent No.: US 7,450,724 B1
(45) Date of Patent: Nov. 11, 2008

(54) HEARING AID ADJUSTMENT DEVICE

(75) Inventor: Michael Greminger, Zürich (CH)

(73) Assignee: Phonak AG, Stafa (CH)

( * ) Notice: Subject to any disclaimer, the term of this patent is extended or adjusted under 35 U.S.C. 154(b) by 0 days.

(21) Appl. No.: 09/385,651

(22) Filed: Aug. 27, 1999

(30) Foreign Application Priority Data

Aug. 17, 1999 (CH) .................... PCT/CH99/00379

(51) Int. Cl.

*H04R 29/00* (2006.01)
*H04R 25/00* (2006.01)
*A61B 5/00* (2006.01)
*A61B 5/12* (2006.01)
*A61N 1/00* (2006.01)

(52) U.S. Cl. .......................... 381/60; 600/559; 73/585; 607/55; 607/56; 607/57; 381/312; 381/313; 381/314; 381/56; 381/58

(58) Field of Classification Search .................. 381/60, 381/312–315, 56, 58; 600/559; 73/585; 607/55–57; 700/94

See application file for complete search history.

(56) References Cited

U.S. PATENT DOCUMENTS 3,809,811 A * 5/1974 Delisle et al. ................. 73/585
4,548,082 A * 10/1985 Engebretson et al. ......... 73/585
4,807,208 A * 2/1989 Geiger .................... 369/30.89
6,674,867 B2 * 1/2004 Basseas ...................... 381/314

FOREIGN PATENT DOCUMENTS

| | | | |
|---|---|---|---|
| DE | 297 06 627 | U1 | 7/1997 |
| EP | 0 661 905 | A2 | 7/1995 |
| EP | 0 814 472 | A2 | 12/1997 |
| WO | WO 85/00509 | | 2/1985 |
| WO | WO8500509 | A1 * | 2/1985 |

* cited by examiner

*Primary Examiner*—Vivian Chin
*Assistant Examiner*—Devona E. Faulk
(74) *Attorney, Agent, or Firm*—Pearne & Gordon LLP

(57) ABSTRACT

A hearing device fitting device that includes a computing device (3), connected on an input side with a connection (E3) for data entry and on an output side with a connection (A3) for a hearing device. The hearing device fitting device further includes an audio storage medium play-back unit having a control input (E9) connected to a computing device (3) output and having an audio output (A3) connectable to a loud speaker unit (11) input. The device supports a method a method for fitting the hearing device in situ by applying the hearing device to an individual; subjecting the individual to an audio test signal; having the individual appraise said audio test signal; and automatically selecting, in dependency of said appraising, a subsequent audio test signal.

12 Claims, 4 Drawing Sheets

HEARING AID ADJUSTMENT DEVICE

The present invention concerns a hearing aid adjustment device according to Claim 1.

BACKGROUND OF THE INVENTION

In hearing aid technology, the tendency more and more is to switch over to processing the audio signals digitally. The transmission of audio signals is effected by means of a digital signal processor unit, ultimately to an electrical/mechanical output coupler of the hearing aid. The transmission performance of the hearing aid between the acoustical/electrical input transformer and the electrical/mechanical output transformer will be constructed on the signal processor unit in such a way that individual hearing deficiencies through the hearing aid will be corrected as extensively as possible.

It is therefore fairly obvious that optimal advantage from such hearing aids can be exploited only if—in steps normally—a preliminary tuning of the hearing aid is made followed by a more precise tuning. During these adjustments the transmission parameters on the hearing aid are adapted to individual needs.

Normally the preliminary tuning occurs by use of diagnostic data, as from audiograms. By means of such data a primary tuning of at least one portion of the transmission parameters is effected on the hearing aid or at least the hearing aid type is selected.

Subsequently, the tuning is done in situ. Generally, an individual for whom one or two hearing aids are to be fitted is equipped with the hearing aids that are to be tuned and is subjected to audio signal tests. A hearing aid has already been applied to the individual mostly on the basis of the individual diagnostic data. The in situ tuning is then further conducted by means of the diagnostic data and/or on the basis of the assessments of the individual concerning practical experience hearing, that is, impressions from everyday life. On the basis of these details it is standard for the acoustics technician to choose one testing signal suitable for testing the individual's assessment from a number of available testing audio signals. This testing signal is presented over loud speaker to the individual with the fitted hearing aid and after a new assessment by the individual a tuning of at least one portion of the transmission parameters is undertaken on the hearing aid.

It is now clear that a manual precision tuning of the transmission parameters on the hearing aids, on the ear of the individual, is not manually feasible—as through a potentiometer operation. Therefore a communication connection to a tuning computer is produced on hearing aids of this type via a corresponding interface.

Based on the assessment by the individual, the computing device determines, among other things by way of a database, which transmission parameters are to be adjusted on the hearing aid and in what manner.

The experienced-based information is stored in the database—which of the aforementioned parameters is to be adjusted and in what manner—according to the aforementioned assessments. Also, algorithmic correlations between parameter settings and assessment will be considered, for example, between an assessment of "too loud" and the loudness increase of the parameters determining the loudness in the hearing aid.

In a more simple case, but not in the most optimal case, the assessment of the individual will result orally through a technician, such as a hearing aid acoustic technician. After the proper conversion, the technician will enter the corresponding data of the assessment into the tuner computing unit with a human input device, normally a computer keyboard.

In order to conduct the tuning procedure in situ as quickly as possible for the individual concerned and as efficiently as possible, a switch-over has been made to standardize individual reactions at least partially and transmit them not via the hearing aid specialists to the tuner computing device but rather directly. Human input devices are used with simple keyboard fields that allow the individual to input data, for example according to a scale. This input unit communicates directly with the tuner computing computer.

The tuning of digital hearing aids occurs increasingly according to psycho-acoustical perception values, and also loudness. Relating to this, reference is made to EP-A-0 661 905 according to U.S. application Ser. No. 08/720,748 of the same applicant as the present application. It is therein explained how the psycho-acoustical perception value "loudness" can be evaluated by an individual by scale and how a computing device, corresponding to the test signal reaction, sets transmission parameters in the hearing aid for the specific critical frequency bands of human hearing. This procedure is described extensively in the aforementioned document and is of importance for the present invention only insofar as it explains how a tuner computing device sets the parameters of the transmission performance in the hearing aid on the basis of scaled loudness indications from the individual.

SUMMARY OF THE INVENTION

The present invention concerns, as mentioned, a hearing aid tuning device of the above named type, primarily independent of how the assessment of the individual is transmitted to the unit, directly or via the interpreting technical knowledge of the specialist. Furthermore, it is not significant for the present invention in what kind and in what manner the tuning device communicating with the hearing aid(s) is connected, e.g., whether by wires or wireless. Independent of these system variants, the present invention concerns the problem, as regards the selection of audio test signals for the individual, that there need be a high level of technical knowledge in the technician undertaking the tuning and/or the problem that the aforementioned audio signals are not optimally chosen according to the corresponding test situation. The present invention undertakes to correct this problem.

This will be achieved through the realisation of the hearing aid tuning device of the above-named type according to the characterisation of Claim 1. Therefore, the invention of the tuning device will comprise an audio storage medium/play-back unit, the control inputs of which are connected with an output of the computing unit and the audio output of which is connected with a connection port for a loud speaker unit.

It will be therefore achieved that the selection of presented audio test signals may best result according to the situation. Because the provided audio storage medium/play-back unit of the computing unit will be controlled, it will be possible to undertake automatically and optimally the selection of the next audio test signal to be presented, according to each assessment—also if necessary according to diagnostic data.

The audio storage medium/play-back unit can be of whatever kind of unit, can contain also in particular one or more memory chip(s) for audiosignals or a CD ROM unit, but nowadays it is effected preferarably with a unit that plays audio CDs.

Now, in particular, during use of a play-back unit, in which audio storage media not originally intended for the unit can be used (as for example CDs of other intended uses regarding hearing aid tuning in an audio CD play-back unit) it is proposed according to the wording of Claim 3, that a testing unit be provided that tests an audio storage medium with regard to a prescribed designation and, consequent to a lack of recognition, stops the play-back unit and preferably gives an indication on a display unit. The aforementioned designation can be of whatever type, for example in the form of a line code. In particular the kind of aforementioned designation is dependent on which category the play-back unit comes under and which kind of audio storage medium is subsequently played.

If, as preferred, an audio CD play-back unit is used, then preferably and according to the wording of Claim 4, the time length data of at least one of the tracks on the CD will be conducted from an output of the play-back unit to a decoder unit of the computing unit that will generate at its output a control signal for the operation of the play-back unit, according to the track time-length data. Through this procedure, in which track length data are utilized generally as coding for play-back operation, it is possible, in pure audio CDs, that is to say, not hybrid CDs, to encode audio storage-conforming information.

Preferably track length data from tracks on the audio CD will be used that is not intended for the play-back of test signals. Thus time length data from the tracks can be utilized that also contain audio test signals. This is so because the time play length of audio test signals is not critical. It can be entirely irrelevant whether an audio test signal and hence the corresponding track lasts 13 seconds or 15 seconds. But the 2 seconds of difference can define the various play-back operation tunes in the sense of the aforementioned coding. However, the aforementioned time length coding is preferably provided on the audio test signal track only when it is certain that the audio track in question, when the coded information is required, is also played back.

This can be the case for example in an audio track that is to be played back for each tuning procedure.

With a view towards the above-mentioned designation for the determination of play-back admissability, Track Number 20 will for example be established therefore with a length of 11 seconds.

The audio CD coding technology above-mentioned and specified in Claim 4 allows for further data to be encoded flexibly. For the testing of speech comprehensibility it is possible to implement on one and the same audio CD speech audio test signals in multiple languages. The tracks arranged for the individual languages will be grouped in track groups. The indication of how many track language groups are included on one audio CD, and how many tracks each group comprises will be gathered on the CD through consistent follow-up of the information coding through track time lengths and will be accordingly selected and interpreted.

With the automated presentation of the audio test signals according to the invention, it is furthermore extremely important to calibrate the loudness level of the presented signals according to an operating point of the hearing aid with respect to loudness. How the audio signal given off from a loud speaker unit is received ultimately by the hearing aid is also dependent on head position and distance between the loudspeaker unit and the individual.

In order to solve this problem, it is proposed in accordance with the wording of Claim 5 that a hearing aid connected to the tuning equipment contain a level detector that is connected with the acoustical/electrical input transformer of the hearing aid. The computing unit is then connected with a release control input for the level detector, and the level detector is connected on the output side with an input for the computing unit. The computing unit thereby controls when the output of the level detector is functionally connected with the computing unit. The input of the computing unit, by which the level detector functions, when activated, on the output side, is connected with a set level comparative unit. With this, it can be detected whether the loudness value detected in situ on the hearing aid correlates to a set value. The output of the set level comparative unit is connected with a level location input for the audio output of the play-back device. The computing unit controls the play-back device for playing back a predetermined calibration storage sector and produces the functional connection of the level detector output to the computing unit.

On the predetermined calibration storage sector of the storage medium that has been mentioned above, a calibration audio signal is stored, in relation to which the set value or set level is implemented that is compared on the comparative unit with the momentary value. Since this sector—a calibration track on an audio CD—is to be played anyway, it is very suitable as a track with an aforementioned coding in its duration.

So that now automatically the test audio signal can be presented in each case correctly and optimally chosen to the individual fitted with the hearing aid, the connection for the human input device on the tuning unit is connected to a selection unit on the computing device. The output of this computing unit functions on a selection input on the play-back unit. On the selection input the storage sector following in each case is selected and controlled. Therefore the connection is always created between the human input device and each audio test signal to be selected.

In a further development the selection unit exhibits a test signal/reaction sample storage unit, preferably in the form of a read-only unit. A number of different samples of signals are pre-stored that correspond to possible test signals, possible reaction signals or assessments of the human input unit. Each of these test signals/reaction signal samples establishes a subsequent test signal then to be activated.

The output of the aforementioned storage unit, controlled—preferably—cyclically, is connected with a comparative unit. The connection for the human input device is connected with the second input of the aforementioned comparative unit. If an assessment of a test signal from the human input device consequently exists, it will be determined in the comparative unit; with such a sample of reactions or assessments as regards the current test signal, the existing reactions/test signal situation concurs or at least correlates. If this pattern which is stored on the test signal/reaction signal sample storage unit is recognized, the corresponding audio storage medium segment, optimal for this sample, will be activated for the generation of the following test signal, since the output of the comparative unit functions on the output of the selection unit—this according to claim 7.

In a further preferred model, the test signal/reaction sample being used at that moment will not only be compared with the pre-stored patterns, but also it will be possible to incorporate the test records so that pattern history storage units may be connected to the links of the comparative unit, according to Claim 8.

In a further preferred model a controlled decoder is connected to the connection for the human input device.

The advantages of the implementation of such a decoder shall be below explained further by means of detailed description. Beforehand it must be presumed that for the parameter tuning on the hearing aid, ultimately standardized assessment criteria on the computing unit will exist. If the assessment data entry, in particular, coming directly from the individual, is undertaken with assessment terms of everyday speech, as with terms "too "too muffled," "too shrill," etc, then one or more situations on the output side will be determined via a decoding table, with the mentioned decoding unit to which signals corresponding to these terms will be directed. These situtations are defined through psycho-acoustical normative terms and allow on the one hand, in the sense of the present invention, an automatic recourse to provided audio test signals, and on the other hand, they allow a placement of parameters on the hearing aid.

The decoding will follow from experienced values.

BRIEF DESCRIPTION OF THE DRAWINGS

The present invention further concerns a process for the tuning of a hearing aid according to the wording of Claim 10 as well as an audio CD according to the wording of claim 11.

The invention will be explained further by means of diagrams. These show.

DETAILED DESCRIPTION OF THE PREFERRED EMBODIMENTS OF THE INVENTION

For now it should be emphasized that all the following sample examples allow the technican many system realization variants. Also for electronic detail realization of the proposed sample forms, there are many possiblities open to the technician.

Figure 1:
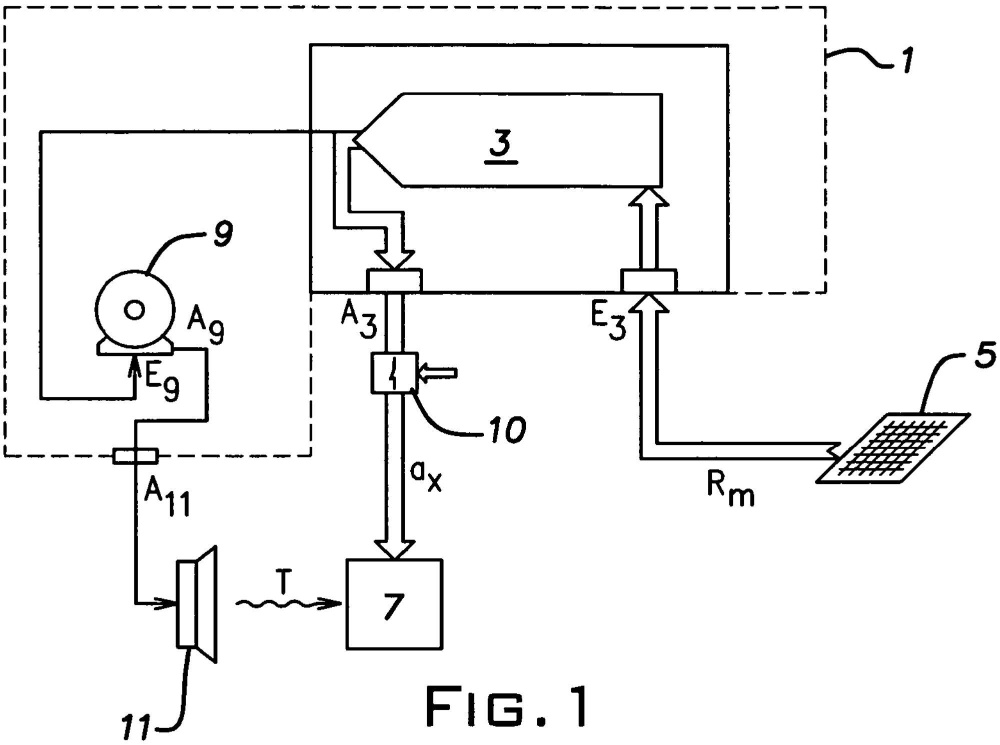
FIG. 1 Overview of signal/function block chart of the tuning device in relation to the invention.

According to FIG. 1 the hearing aid tuning device 1 contains a computing unit 3, which functions on the output side on a connection A3 for one or two hearing aids 7. The computing unit 3 further exhibits, on the input side, a connection E3 for a human input device 5, whether this be a common keyboard, a keyboard with fewer scaling keys, a speech input unit, a mouse, a joystick, etc.

On the output side the computing unit 3 is connected further with the control inputs E9 of an audio storage medium play-back unit 9, the audio output A9 of which is connected or can be connected with a loud speaker unit 11 via a connection A11, by means of which test signals T are transmitted to the hearing aid 7 fitted in situ.

The device depicted in FIG. 1 basically functions as follows:

The individual with the fitted hearing aid 7 is subjected to a test signal T. Through direct manual entry or through oral reporting to a technican and subsequent entry, the reaction or assessment of the individual to the test signal T is fed via the human input device 5 to the computing unit 3 of the tuning device 1.

Figure 2:
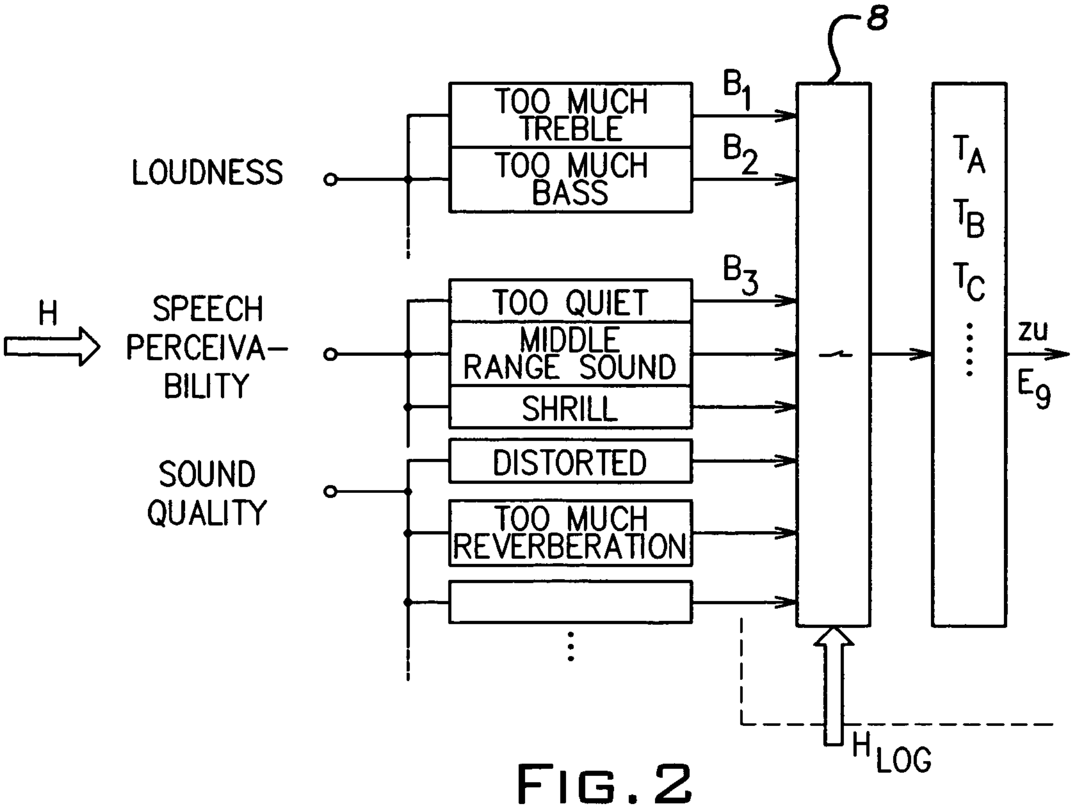
FIG. 2 in the form of a simplified signal/function block flow chart, a preferred selection technology for test signals in the device according to FIG. 1.

In FIG. 2, a primary sample variant is depicted of how, viewed in combination with FIG. 1, the play-back unit 9 is controlled by the computing unit 3. It describes H "manual entry." On the basis of the assessment of any individual in relation to the individual's hearing with a hearing aid to be tuned, a hearing aid acoustic technician preferably will convert the assessment in psycho-acoustic terms, as for example in relation to loudness, comprehensibility and sound quality. The technician will enter the scaled responses according to the individual assessment, as with regard to loudness "too high," etc, as with regard to comprehensibility "too shrill," as with regard to sound quality "too much echo."

This input is fed into a selection unit 8 with the corresponding scaled response. In the simplest case, the selection unit 8 of each converted assessment B1, B2 . . . will allocate an assigned audio test signal T according to the manual entries.

Since one and the same audio test signal T optimally can be allocated to multiple assessments B and, in a further development of the invention, the test signals T on the basis of logical operations such as AND, OR, etc, can be allocated by B assessments, a selection unit 8 is preferably provided—and as in FIG. 2 depicted—, to which selection unit 8, on the one hand, the assessment signals B are directed, and on the other hand—as depicted with Hlog—the logical operation type can be entered, with which type the assessment data B is to be joined and which initiate each test signal T optimally for the existing assessment combination on the output side.

Looking back at FIG. 1, the play-back unit 9 will be consequently controlled by the computing unit 3 on the basis and according to the assessment of corresponding entries Rm via the control input E9 for the play-back of a chosen audio test signal. The test signal T will be played via a loud speaker unit 11.

The chosen audio test signal T will be played preferably in a loop or repeated, and as depicted in FIG. 1 with the switch unit 10—the technician will switch on the parameter tuner on the hearing aid 7 manually, with which tuning device the transmission of the hearing aid will be adjusted appropriately by the computing unit 3 and according to the standard of the current assessment signal B according to FIG. 2.

The manual entry according to H of FIG. 2 occurs via the connection E3 for the human input device 5 of FIG. 1.

Figure 3:
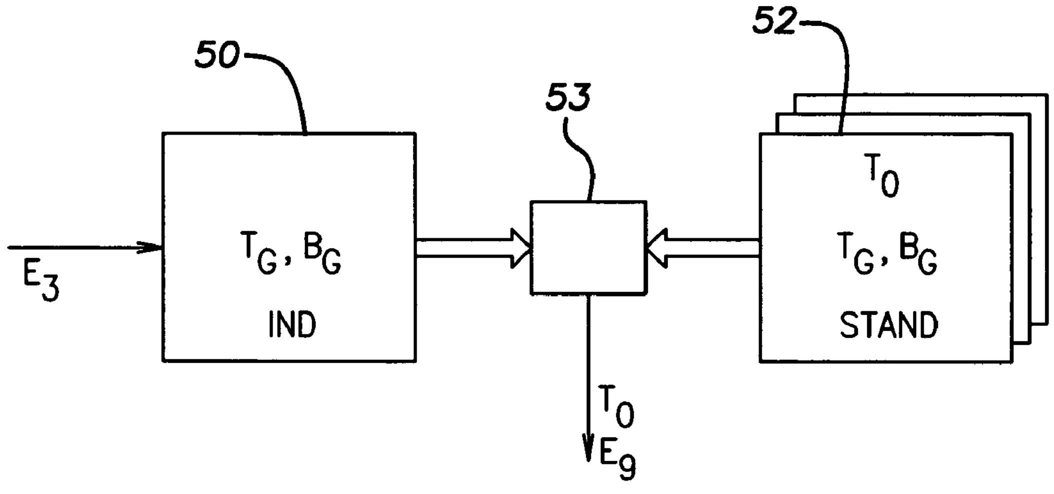
FIG. 3 in the form of a simplified signal/function block flow chart, a further possibility to select a subsequently playing test signal, with a procedure in relation to the invention according to FIG. 1.

In FIG. 3, by means of a simplified function block/signal flow chart, a further development is depicted of the previously explained device in relation to the invention or of the tuning process in relation to the invention. A storage unit 50 for the individual is provided on the computing unit 3 as well as a standard storage unit 52. In the storage unit 50 for the individual, the audio test signals T3 experienced during the in situ tuning procedure and, therefore coupled together, the individual assessments experienced will be stored according to the entry signals to E3 of FIG. 1 and will be continually expanded during the procedure. Consequently, the tuning procedure experienced up to that point is stored in this storage device 50. Analogously, a number of possible test signal and assessent records can be stored in the standard storage unit 52 as a database, together with the respective identification of a following audio test signal TO, which has been found in the respective records as optimal for a further tuning step. The data has been determined in the standard storage unit 52 through experiments and experience and stored in the unit 52 in the preferred form of read-only. According to FIGS. 1 and 2, at this point of the present input for the assessment of significant quantities according to B of FIG. 2, a dating occurs of the individual storage device 50. The tuning record, stored in the individual storage device 50, is now compared on a comparative device 53 with the standard tuning records stored in the standard storage unit 52, and it is then determined which one accords best with the one stored in the individual storage device 50 at the moment. As a result, the audio test signal TO assigned and optimally as the one to be played next will be selected by the record found from the standard storage unit 52, and according to FIG. 1 the assigned medium sector will be controlled on the control input E9 of the play-back unit 9.

In this way, the process according to the invention basically enables, according to FIG. 1, the automatic setting off directly of audio test signals T to be played after assessment input and/or in refined form with consideration of already experienced individual tuning steps.

Some additional preferred functions of the tuning device 1 in relation to the invention presented in principle by means of FIGS. 1 to 3 will be considered more closely.

Figure 4:
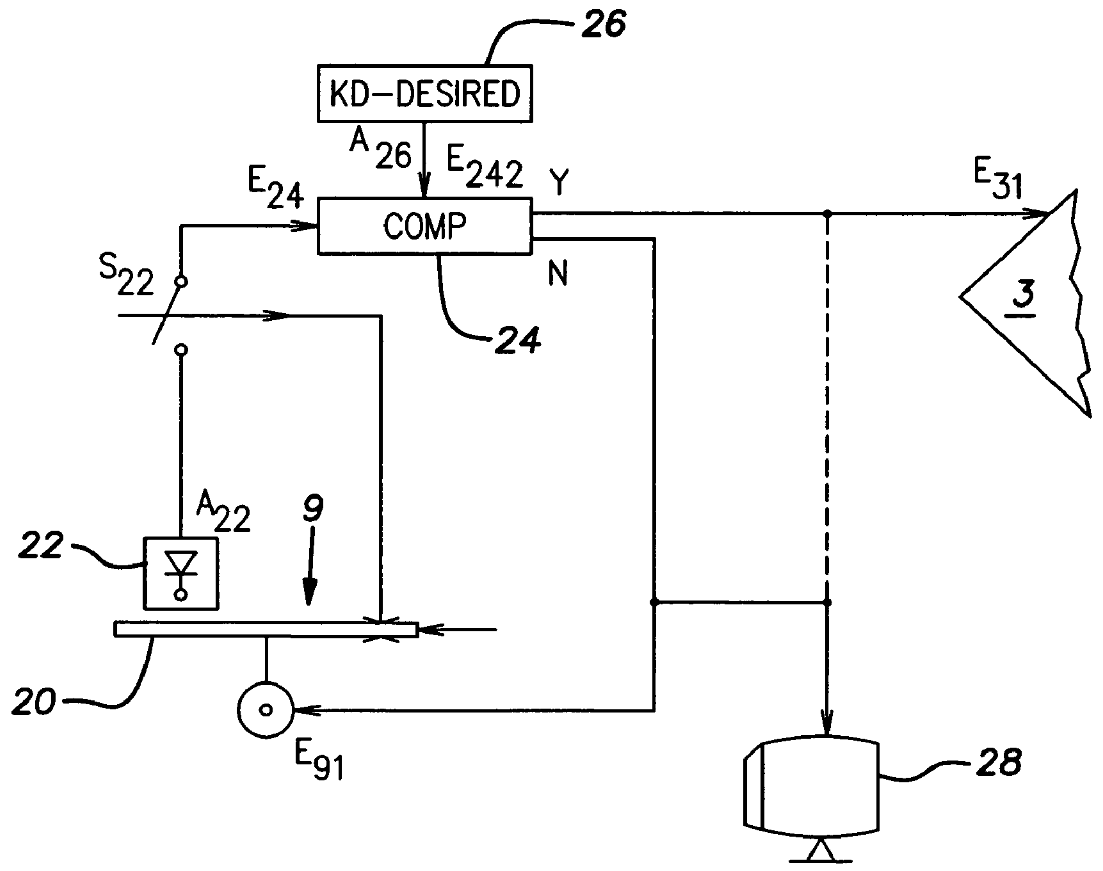
FIG. 4 in the form of a simplified signal/function block flow chart, with measures for the hinderance of playing audio storage media not suited to this purpose according to FIG. 1 on the tuning device in relation to the invention.

In particular with the use of a play-back unit 9, to which storage media 20 can be directed that are not specific to hearing aid tuning, according to FIG. 4, during retrieval of the audio storage medium 20 in the play-back unit 9, the output A22 of an indicator detector 22—as shown with the switch S22—is directed to an input E24 of a comparer unit 24, to the second comparer input E242 of which, the input A25 of a set value marker storage device 26 is directed. If the indicator KZ registered by means of the detector 22 does not accord with the one previously stored in the storage device 26, then the play-back of the medium 20 just entered will be blocked in a control input E92 of the play-back unit 9, if necessary the medium will be ejected and the situation will be indicated in a display unit 28. If the detected indicator KZ accords with the set value sign KZ-SOLL, then a signal will be transmitted by the output Y of the comparer unit 24 to an input E32 of the computing unit 3, and if necessary of the display unit 28—as represented in shading—whereby the tuning procedure can begin.

As indicators, which are to be recorded with the detector 22, information will be provided in a preferred manner on the medium 20, which will be selected with the same device as afterwards are the audio signals. With an audio CD, the indicator information will be consequently gathered as preferably audio information on the medium 20 and selected as first with the introduction of a CD.

Although it is possible to provide coding with an audio CD today utilized as a playing medium through gathered audio signals—for example selective frequency—a preferred coding technique treated in itself in relation to the invention will be explained further by means of FIG. 5, which will show the structure of an audio CD in relation to the invention.

Figure 5:
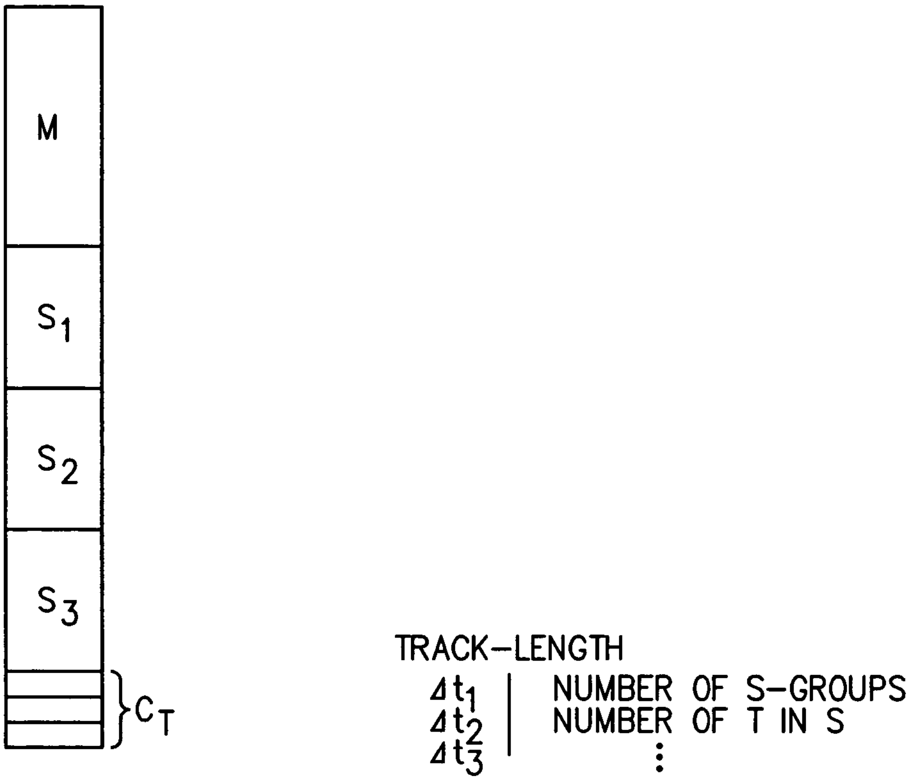
FIG. 5 schematically, the structure of a coded audio CD in relation to the invention.

An audio CD in relation to the invention, represented in its track structure in FIG. 5, contains a first group M of tracks, which comprise audio test signals that are not language specific, for example music, sounds, etc. The CD contains further one or more groups (n) S1, S2 . . . of tracks, which contain group specific language recognition test signals in corresponding number of different languages. Therefore for example the group S1 is constructed through German-speaking tracks, group S2 through English-speaking tracks, etc.

The CD in releation to the invention contains now further one or more coding track(s) Ct, which at least partially can contain audio test signals; this is however an exception.

It is essential that—as usual with the remaining tracks on the CD and with each audio CD player—the time lengths Δt of the respective tracks are selected and are given to an output according to FIG. 4 corresponding to A22. As is displayed in FIG. 5 tabularly, the length of the tracks CT is gathered together so that this length contains information for the operation of this CD. The track length for example Δt2 on a CT track Number 1 of 15 seconds means that four language groups S are provided on the CD, a track length of 14 seconds so that only four groups are provided, etc. On a further CT track for example a length Δt2 of 15 seconds means that in each of the language groups S five tracks are provided, for the of length 14 seconds, only four tracks are provided etc.

Looking back at the problem addressed above concerning CD recognition, it is clear that one of the CD tracks will be used with a preset length and that each audio CD will be ejected as inadmissable whose corresponding track does not have a preset length. The introductory loudness calibration track already described that is to be played in any case for example can be used.

In this manner, it is possible most flexibly to change the CDs in relation to this invention and to encode the necessary information for the play-back operation on the CDs without the use of some foreign coding means for the production of audio CDs.

Before test signals are now emitted it is practically necessary to calibrate the loudness level to the operating point of the hearing aid 7. Under consideration of FIG. 1, it is perceptible that this should result because, for instance, the distance between loud speaker unit 11 and hearing aid 7, head position and ear formation etc. of the individual has an effect on the loudness level received in the hearing aid 7.

Figure 6:
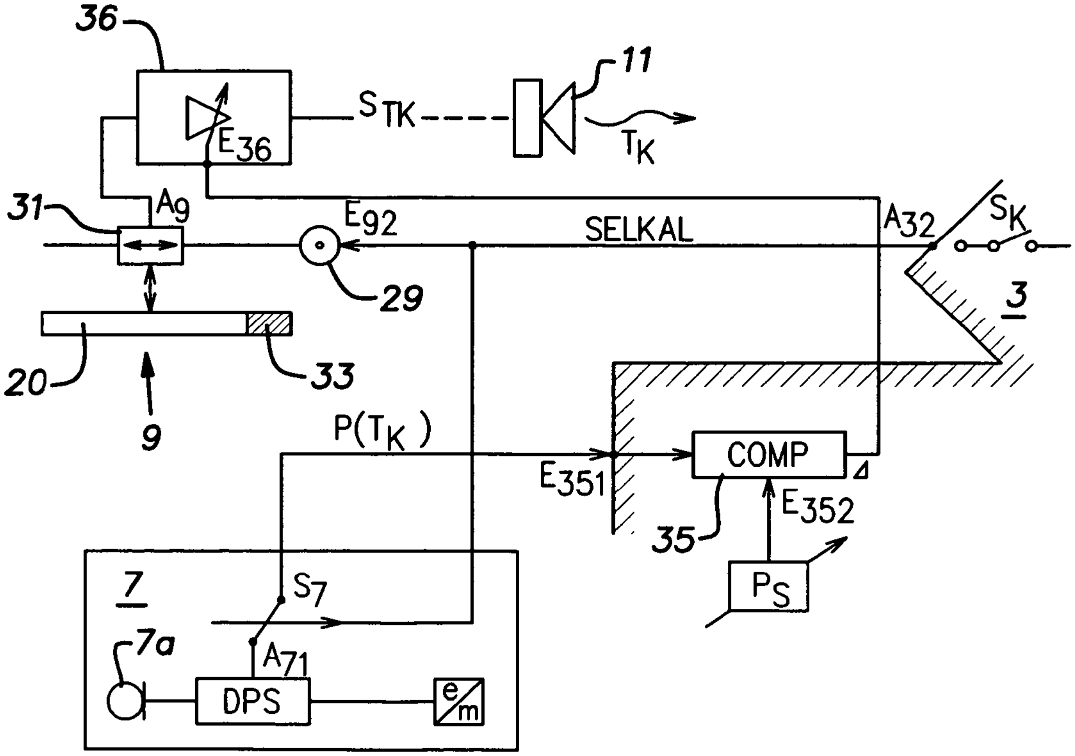
FIG. 6 in the form of a simplified signal/function block flow chart, with measures in the device in relation to the invention according to FIG. 1 or FIGS. 1 and 2 for the calibration of the audio test signals automated in relation to the invention as regards level of loudness, and FIG. 7 in representation analogous to FIGS. 1 to 6, with measures for the decoding of simple reaction entries in standardized multiple signals in the device in relation to the invention.

The calibration procedure explained by FIG. 6 can be initiated each time through manual entry to the computing unit, also between two audio test signals T. Initiated by the calibration switch Sx depicted in FIG. 6, the computing unit 3 emits a control signal SELKAL to an output A32 to the play-back unit 9, to a control input E92, which signal positions a drive 29 for the selection unit 31—as depicted—on a pre-determined calibration storage sector 33 of the medium 20. The calibration test signal Tx is transmitted by this sector 33 to the loud speaker unit 11 and is transmitted to the hearing aid 7 depicted enlarged in FIG. 3 on the ear of the individual.

On the digital signal processor unit DPS of the hearing aid 7, a level detection stage (not depicted explicitly) is planned that will emit an audio signal P(Tk) independent of a momentary loudness level to an output A71. At the same time with the production of a functional connection between output A71 of the level detector and the computing unit 3—depicted with the closing of the switch S7—the computing unit 3 controls the play-back of the calibration sector on the medium 20. The level signal P(Tx) is set into the input E351 of a calibration comparative unit 35. A set value level detector Pa is directed further to the comparative unit 35, to a second input E352. The comparative result or the comparative difference Δ will be directed to the amplification control input E36 of an amplifier stage 36 provided in the audio signal path of a play-back unit/loudspeaker unit, at which stage, if necessary in a regulating sense, the amplification will be adjusted repeatedly until the calibration test signal Tx received from the hearing aid 7 corresponds to the set value P3 and therefore to the loudness operating point of the hearing aid 7.

By means of FIG. 2 in combination with FIG. 1, it has been explained how an audio test signal T ultimately is chosen and emitted though entry and weighted-response of psycho-acoustical terms—derived from the assessment of the hearer's experience, directly or through implementation of logical combinations of assessment values B.

Figure 7:
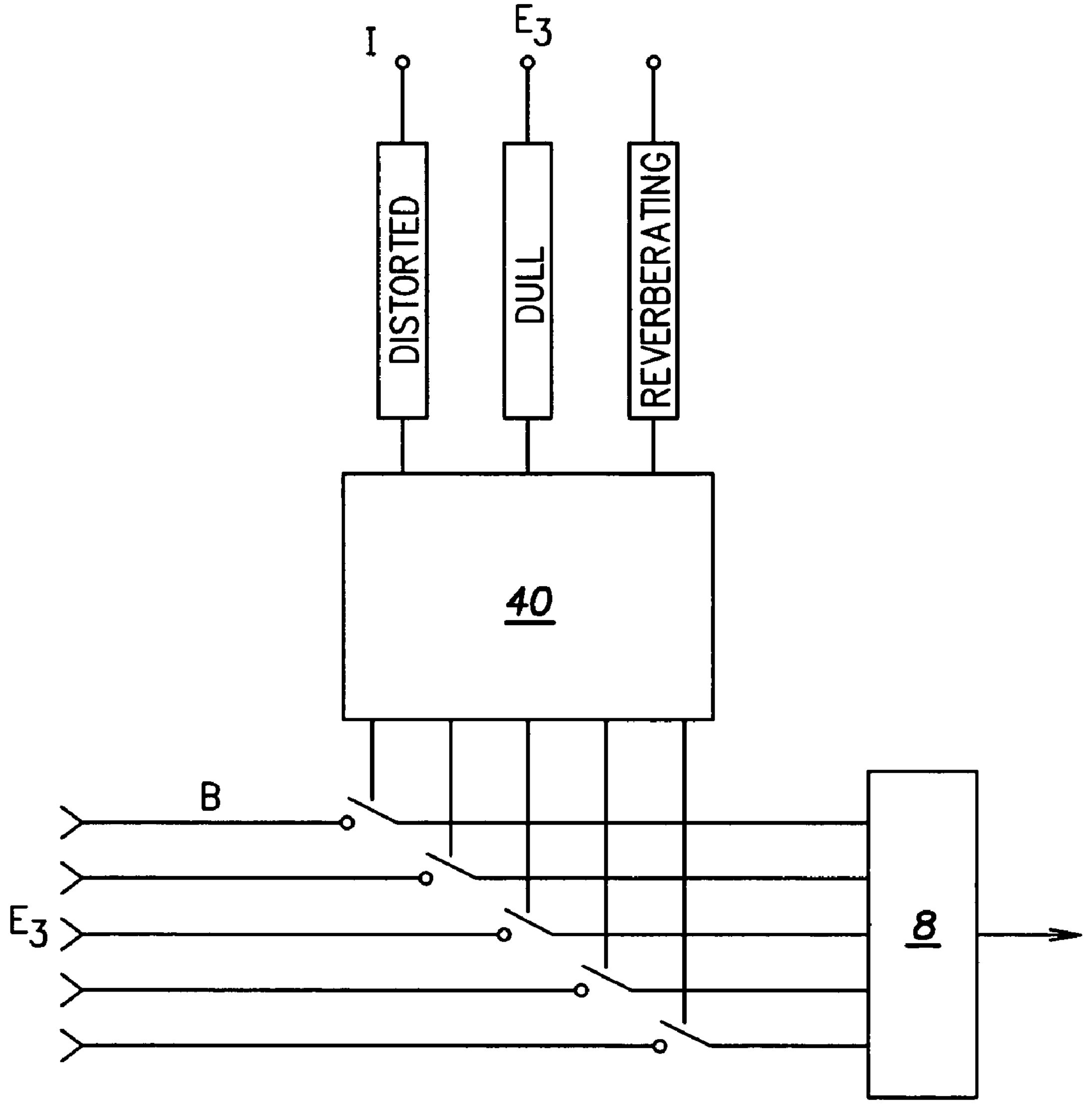

In particular, when it is sought that the individual shall enter the assessments data directly into the computing unit— according to FIG. 1 to E2—then this procedure is to be refined, since the individual is not trained to convert the hearing results into the aforementioned weighted, standardized psycho-acoustical values. Here, as it shall be explained by means of FIG. 7, a decoding unit will be supplied on the computing unit. The depiction follows from the process (able to be toggled) whereby data entry is possible via the technician, according to FIG. 2, as well as via the individual. In FIG. 7 the signal paths B indicate the assessment quantities already explained by means of FIG. 2 and weighted and entered by the technician. Also shown are the I individual assessment quantities entered in input E3 with a view to FIG. 1, as for example "echoic," "muffled," "distorted."

On the computing unit 3 according to FIG. 1 a decoding unit 40 is supplied, wherein it is pre-stored in the form of a decoding table, with which standardized psycho-acoustical evaluation quantities, according to B, are represented. For example, the individually entered term "distorted" can mean that the loudness is too high and/or the comprehensibility too shrill and/or the sound quality distorted. On the output side of the decoder unit 40, the psycho-acoustical evaluation quantities according to B are linked through to the selection unit 8 according to FIG. 2; these quantities best represent the individually entered evaluation criterion in a psycho-acoustical manner. The selection unit 8 controls the play-back of the corresponding optimal audio test signal, as previously explained.

The connection E3 for the human input device 5 is connected with the decoding unit 40, which produces output data to a decoding unit output that is connected with the computing unit 3 on its input side and preferably is also connected with a display device. The output data provided to the decoding unit output is produced from input data I from the human input device, according to stored decoding tables.

With the tuning device in relation to the invention it is possible to tune hearing aids economically and in an extremely goal-oriented way, in particular to fine-tune. In consideration of various auditory practices, for example according to different language regions, in each case adapted audio storage media can be implemented, or test signals can be provided in different languages on one and the same storage medium that in each case are selected through initial language selection in a controlling data input device.

What is claimed is:

1. An apparatus for fitting a hearing device which is worn by an individual, said apparatus comprising:

a data entry device;

a computing device connected on an input side with a connection for connecting to said data entry device and on an output side with a connection for a hearing device adjusting input, an audio storage medium play-back unit storing a plurality of audio tracks with audio test signals and having a control input connected to another output of said computing device and having an audio output connectable to a loud speaker unit input, and a storage device for storing a plurality of individual assessment data and audio test signals experienced by the individual, wherein said individual assessment data is entered into said data entry device based on perceptions of said individual wearing said hearing device and listening to one of said audio tracks, said individual assessment data and said audio test signals experienced by the individual being stored in said storage device, and further wherein said computing device computes a control signal based on said stored plurality of individual assessment data and said stored audio test signals experienced by the individual, wherein said control signal is applied to said other output of said computer device, and said control signal is used for automatically selecting another one of said audio tracks.

2. The apparatus for fitting a hearing device according to claim 1, wherein said playback unit contains at least one audio storage chip.

3. The apparatus for fitting a hearing device according to claim 1, wherein said playback unit is a CD playback unit.

4. The apparatus for fitting a hearing device according to claim 1, further comprising a comparer unit that tests the audio storage medium in said playback unit for a predetermined identification and which disables said playback unit on non-recognition of said predetermined identification.

5. The apparatus for fitting a hearing device according to claim 1, further comprising a decoding unit, wherein said playback unit is an audio CD playback unit generating a specification of an extent of at least one of the segments on the audio storage medium in said playback unit, and wherein said specification is fed from an output of said playback unit to said decoding unit which then generates a control signal for the operation of said playback unit.

6. The apparatus for fitting a hearing device according to claim 1, wherein said fitting device further comprises a set-level comparative unit having an output operationally connected to a level control input of said playback unit for controlling said audio output, wherein the hearing device is connected to said hearing device output, the hearing device having a level detector which is connected to an acoustical/electrical converter of the hearing device, such that said computing device generates, on a level detector control output, a level detector control signal for controlling an operational connection between a level detector output of said level detector and a computing device control input of said computing unit, said computing device control input also operationally connected to said set-level comparative unit, and wherein said computing device enables said playback unit for playback of a predetermined storage segment of the audio storage medium upon receipt of a control signal on said computing device control input, and further wherein said computing unit controls establishing said operational connection of said level detector output to said computing device control input.

7. The apparatus for fitting a hearing device according to claim 1, said computing device further including a selection unit, wherein said connection for data entry is connected to a human input device and is operationally connected with said selection unit, a selection output of said selection unit being operationally connected to said selection input of said playback unit.

8. The apparatus for fitting a hearing device according to claim 7, wherein said selection unit has a test signal/reaction signal pattern storage unit, an output of which is operationally connected to a first input of a comparing unit, said connection for data entry being operationally connected with a second input of said comparing unit, said comparing unit having an output operationally connected to said control input.

9. The apparatus for fitting a hearing device according to claim 1, wherein said connection for data entry is connected to a human input device and to a decoding unit which generates, from input data from said human input device, according to stored decoding tables, output data to an output of said decoding unit that is operationally connected with another input of said computing device.

10. A hearing device fitting arrangement comprising:

an audio storage medium playback unit including:

an audio storage medium having a plurality of storage segments each for storing audio test signals representing common daily experiences;

a control input having a selection input for selecting any of said plurality of storage segments; and an audio output;

a loudspeaker operationally connectable to said audio output of said playback unit;

a storage device for storing a plurality of assessment data and audio test signals experienced by the individual; and a computing unit including:

a data input for data entry by an individual carrying said hearing device to be fitted, said data input for said individual to input said assessment data for assessing said hearing device during playback of one of said storage segments for storing in said storage device, a hearing device output for operationally connecting to the hearing device, and an audio control output for operationally connecting to said control input of said audio storage medium playback unit;

wherein said computing unit is adapted to compute a control signal for said audio control output in dependency upon said stored plurality of assessment data and said stored audio test signals experienced by the individual, thereby automatically selecting another one of the plurality of storage segments.

11. The hearing device fitting arrangement according to claim 10, wherein said connection for data entry is connected to the human input device via a decoding unit which generates, from input data from said human input device, according to stored decoding tables, output data to an output of said decoding unit that is operationally connected with another input of said computing unit.

12. A hearing device fitting device comprising:

an audio storage medium playback unit including:

a control input having a selection input for selecting one of a plurality of storage segments on an audio storage medium, wherein said storage segments each include audio signals representing common daily experiences; and an audio output;

a loudspeaker operationally connectable to said audio output of said playback unit;

a storage device for storing a plurality of assessment data and audio test signals experienced by the individual; and a computing unit including:

a data input for data entry of said assessment data by an individual carrying a hearing device to be fitted for storing in said storage device, a hearing device output for operationally connecting to the hearing device for programming said hearing device, and a audio control output for operationally connecting to said control input of said audio storage medium playback unit;

wherein said computing unit computes a control signal to said audio control output in dependency upon said stored plurality of assessment data and said stored audio test signals experienced by the individual for automatically selecting one of said plurality of storage segments depending on signals applied to said data input.

* * * * *